(12) United States Patent
Chiou et al.

(10) Patent No.: US 9,724,692 B2
(45) Date of Patent: Aug. 8, 2017

(54) MULTIPLEX SLIDE PLATE

(71) Applicant: Quark Biosciences, Inc., Hsinchu County (TW)

(72) Inventors: Chung-Fan Chiou, Hsinchu County (TW); Chao-Chi Pan, Hsinchu (TW); Cheng-Wey Wei, New Taipei (TW); Yu Chang, Taipei (TW)

(73) Assignee: Quark Biosciences, Inc., Hsinchu County (TW)

( * ) Notice: Subject to any disclaimer, the term of this patent is extended or adjusted under 35 U.S.C. 154(b) by 600 days.

(21) Appl. No.: 13/928,396

(22) Filed: Jun. 27, 2013

(65) Prior Publication Data

US 2015/0005203 A1 Jan. 1, 2015

(51) Int. Cl.
*B01L 3/00* (2006.01)
*C12Q 1/68* (2006.01)

(52) U.S. Cl.
CPC .......... *B01L 3/50851* (2013.01); *C12Q 1/686* (2013.01); *B01L 3/5025* (2013.01); *B01L 3/50857* (2013.01); *B01L 2200/16* (2013.01); *B01L 2300/0819* (2013.01); *B01L 2300/0858* (2013.01); *B01L 2400/0677* (2013.01)

(58) Field of Classification Search
None
See application file for complete search history.

(56) References Cited

U.S. PATENT DOCUMENTS

| | | | |
|---|---|---|---|
| 4,970,053 A | 11/1990 | Fechtner | |
| 5,710,381 A * | 1/1998 | Atwood | G05D 23/1935 422/550 |
| 5,985,218 A | 11/1999 | Goodale | |
| 6,149,872 A | 11/2000 | Mack et al. | |
| 6,235,471 B1 * | 5/2001 | Knapp | B01L 3/0262 435/283.1 |
| 6,716,629 B2 | 4/2004 | Hess et al. | |
| 6,893,877 B2 | 5/2005 | Hunter et al. | |
| 7,307,802 B2 | 12/2007 | Unger | |
| 7,332,271 B2 | 2/2008 | O'Keefe et al. | |
| 7,588,672 B2 | 9/2009 | Unger et al. | |
| 7,614,135 B2 * | 11/2009 | Santini, Jr. | A61B 5/00 29/595 |
| 7,666,360 B2 | 2/2010 | Schellenberger et al. | |
| 7,682,565 B2 | 3/2010 | Linton et al. | |
| 2003/0124716 A1 | 7/2003 | Hess et al. | |
| 2004/0187951 A1 | 9/2004 | Barker | |
| 2006/0003347 A1 * | 1/2006 | Griffiths | C12N 15/1075 435/6.12 |
| 2007/0074972 A1 | 4/2007 | Nassef et al. | |
| 2007/0202010 A1 | 8/2007 | Talebpour et al. | |
| 2008/0108112 A1 | 5/2008 | O'keefe et al. | |
| 2009/0117620 A1 | 5/2009 | Fritchie et al. | |
| 2009/0294703 A1 | 12/2009 | Unger et al. | |

FOREIGN PATENT DOCUMENTS

| | | |
|---|---|---|
| CN | 101631502 | 1/2010 |
| CN | 202968546 | 6/2013 |
| WO | 2005028629 | 3/2005 |

OTHER PUBLICATIONS

Leamon et al. (Electrophoresis 2003, vol. 24, p. 3769-3777).*
"Office Action of Taiwan Counterpart Application," dated Mar. 25, 2015, p. 1-p. 5.
Yang Li, "Microwell Array Based Universal Multiplex PCR and Its Application", Dissertation Submitted to Shanghai Jiao Tong University for the Degree of Master, Feb. 2011, pp. 1-70.
"Office Action of China Counterpart Application", dated Apr. 13, 2015, pp. 1-7.

* cited by examiner

*Primary Examiner* — Stephanie K Mummert
(74) *Attorney, Agent, or Firm* — Jianq Chyun IP Office (57) ABSTRACT

The present invention relates to a multiplex slide plate for various types of assays. The slide plate may be pre-filled with special-formulated reagents in different reaction zones, and the reactions carry out independently in the reaction zones filled with special-formulated reagent.

10 Claims, 10 Drawing Sheets

MULTIPLEX SLIDE PLATE

BACKGROUND

Technical Field

The disclosure relates to a test slide. Particularly, the disclosure relates to a multiplex slide plate prefilled with polymerase chain reaction reagent(s).

Related Art

In the field of molecular biology, a variety of different experiments or test methods may be required to investigate the specific sample. For example, in the DNA assay, it is common to test a sample for several single-nucleotide polymorphism (SNP) genotypes, or the expression levels of a number of genes via polymerase chain reaction (PCR) assays. Several DNA assays may compose of a test panel for diagnosis, such as several PCR assays form a cancer diagnostic test panel. A PCR assay comprises at least two DNA specific primer probes (for some PCR also include additional target specific reporter probes), and this pair of primers has to correctly mix with the DNA template extracted from the sample to be tested (the sample) so as to examine the presence or the amount of the specific DNA targets in the sample. Traditionally, the pair of primers and the sample are delivered to the same reaction vessel for PCR. The delivery is usually done by pipetting the individual solutions from individual vials which store primer pair, enzyme and reagents, and the sample, to the reaction vessel. The most common vessel format is the 96-well titter plate. In such way, a PCR assay requires at least two pipettings, one for adding the primer pairs and another one for adding the sample to the reaction vessel. For example, for a panel to examine 36 targets in one sample, it needs at least 36 pipettings to add each pair of primers to 36 different reaction vessels, and another 36 pipettings to add sample to each of above vessels. This part of labour work is not only complex and error-prone, but also takes a lot of manpower.

One approach, called multiplexing approach, is to test the sample in the same reaction zone with mixtures of more than one pair of primers. Typically, 2 to 4 pairs of primers are added in one reaction vessel. For example, if 4 primer pairs using one vessel, the above mentioned example of test one sample for 36 targets, would require 9 reaction vessels, and the minimum pipetting needed would be 36 for adding primer pairs plus 9 for adding sample (a total of 45 pipettings). The labour work has been reduced. In spite of the convenience of the multiplexing approach, many reactions are performed simultaneously and the reaction and/or signal detection may interfere with each other to deteriorate the accuracy of the tests. Therefore, it is difficult to go beyond 6 pairs of primers in one reaction vessels.

Another approach is pre-filled primer pairs to individual reaction vessels in the factory. The lab user only needs to add sample to the pre-filled vessels. The above mentioned example of testing one sample for 36 targets would require only 36 pipettings for adding sample to 36 pre-filled vessels. Or even more the process may be further reduced to 9 pipettings, if multiplexing technique is also applied.

Another approach is to reduce the reaction vessel volume of titter plate to nano-liter range to save the cost of reagents. The result format is a slide-like micro-titter plate. The size and volume of reaction vessels (also called micro-wells or nano-wells), in a micro-titer plate are too small to be filled with the primers or sample manually without causing cross contamination between neighbouring vessels (i.e. the primer escapes from one well to other wells).

One approach is to provide the microfluidic chip designed with microfluidic channels, which deliver testing reagents (mainly primer pair) and samples to individual reaction wells for independent reactions. But the microfluidic chip is difficult to design and manufacture, and also adds high cost to the assays.

One approach is to pre-deliver primer pairs to each individual nano-wells in advance and immobilize the primers onto the well inter-surface. Therefore, the user can apply the sample to the wells by one pipetting or through one microfluidic channel without worrying about primers escaping from one well to other wells. The cross contamination between wells is minimized. However, the immobilization restricts the primer movement in the reaction vessel, which greatly reduce the efficiency of PCR.

In summary, if these primers probes may be placed into the reaction zone in advance, it can greatly simplify the labour work. However, as long as the reaction involving two or more reaction zones, the same sample has to be distributed to different zones of individual reactions without causing the pre-filled primers to cross contaminate between the zones.

The most important consideration is that each reaction vessel must be filled with the predetermined amount of sample. However, during filling the sample, the reaction vessels may not be cross-contaminated with reagents of different test assays. The traditional method is to use pipette or needle dispensers to load the sample "one by one" into the reaction wells. As the reaction well volume becomes smaller and the inter-well distance becomes closer, it is a challenge to fill the sample in each well without cross-contamination. Special mechanical mechanism or paths may be needed for the dispenser to reach each reaction well individually, which is complex and time consuming. As for the microfluidic devices designed with micro-channels, the design of the microfluidic devices and micro-pipeline in line significantly increases the production costs.

SUMMARY

The present invention provides a multiplex assay array plate prefilled with reagent(s) for biological, biochemical or chemical assays, particularly, polymerase chain reaction; more particularly, real time polymerase chain reaction. Using the concept of release control, the pre-filled reagent(s) is designed with a special formulation to allow the delayed release of the reagent(s) during the period of filling the sample solution (sample filling period) to the reaction vessel. The pre-filled reagent(s) is subsequently released into the sample solution after the sample filling period is finished and before the starting of PCR. Therefore, the components in the pre-filled reagents (i.e. primers and associated specific reporter) will be fully suspended in the mixture solution and the PCR efficiency will not be deteriorated. But the immobilized-like property before the components in the pre-filled reagents been released, makes the concern of cross-contamination due to the sample filling operation is relieved. With the release control reagent(s) prefilled in the reaction wells, the sample can be loaded through overflow, immersion, capillary suction, vacuum suction, brushing or squeegee over the reaction slide plate, so as to fill all of the reaction wells in a very short time and with one pipetting. The formula or recipe of the prefilled reagent(s) may also make the preservation and/or transportation of the pre-filled test reagent(s) easier.

The present invention provides a multiplex slide plate, including at least a slide plate having a sample loading region and an assay region having a plurality of reaction vessels. The plurality of reaction vessels is arranged in arrays and each of the plurality of reaction vessels has an opening portion and a bottom portion narrower than the opening portion. Each of the plurality of reaction vessels includes a formulation of a prefilled reagent and a controlled-release substance.

According to embodiments of the present invention, each of the plurality of reaction vessels has a slanted sidewall connecting the opening portion and the bottom portion.

According to embodiments of the present invention, the formulation of the prefilled reagent includes at least a pair of primers of a polymerase chain reaction (PCR). Also, the formulation of the prefilled reagent may include a reporter.

According to embodiments of the present invention, the controlled-release substance includes glycerol. The content of glycerol may be 30 wt % or more and the formulation of the prefilled reagent becomes viscous with a gravity sliding rate less than 5 μm/day.

According to embodiments of the present invention, the controlled-release substance includes poly(vinyl alcohol) (PVA), poly(vinyl pyrrolidone)(PVP), polyethylene glycol/polyethylene oxide (PEG/PEO), alginic acid, natural starch or artificial starch.

According to embodiments of the present invention, the controlled-release substance includes polyurethane, agarose or polyacrylamide.

According to embodiments of the present invention, the controlled-release substance includes micron particles of activated carbon or nano-particles of activated carbon.

In order to make the aforementioned and other features and advantages of the disclosure comprehensible, several exemplary embodiments accompanied with figures are described in detail below.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

FIG. 1' shows exemplary cross-sectional views of the reaction vessels of the assay array plate according to embodiments of the present invention.

DETAILED DESCRIPTION OF DISCLOSED EMBODIMENTS

The disclosure relates to a multiplex slide plate or assay array plate, which can be widely applied to various types of reaction assays. The disclosure provides a test slide, either a glass micro-well plate or a plastic micro-well plate, pre-filled with testing reagents for multi-reactions. The test slide piece may be produced with pre-filled testing reagents in different reaction zones, and the reactions carried out independently in the reaction zones filled with special-formulated reagents may be the same or different. This invention also provides a controlled release formulation of the reagents. The formulation of the testing reagent(s) according to the present invention improves the long-term preservation of the reagents and makes transportation and distribution of the reagents easier.

The following descriptions are provided to further define the present invention for illustration purposes.

A reagent may refer to a formulation of several ingredients used for a particular test. For example, in the test using polymerase chain reaction (PCR), the testing reagent includes a pair of primers, enzymes, dNTPs, fluorescent reporters, salts and etc. During application, the different primer pairs and fluorescent reporters may be added to the reaction vessel firstly, and then followed by mixing the enzymes, dNTP, and other additives with the sample to the reaction vessel.

Sample(s) generally refers to the object being tested. For example, the sample may be agricultural specimen, pathological slices, soil specimen or nucleic acid fragments (DNAs or RNAs) extracted from the aforementioned specimen.

Assay(s) or test(s) may refer to one or more assays or test items performed to the same sample. For example, using PCR to check a nucleic acid sample for 300 SNP assay, such assay includes a number of PCR test items by checking each genotype (A, T, C, G) of each SNP. For example, using real time PCR to determine amount of nucleic acid carry a specific sequence. Sample solution or mixture refers to the mixture or solution of the sample mixed with the aforementioned portions of the reagent for the reaction zone.

Reaction vessel may represent the tube, the individual tube(s) of the tube plate, the hole(s) or well(s) in the micro-titer plate, the individual reaction well(s) or pit(s) in the test slide plate or the array plate. As described herein, the "slide plate", "slide piece", "assay array plate" or "assay plate" may refer to the same substrate plate accommodating the reaction vessels.

When the volume of the liquid in the container is reduced to a certain level, the flow of the liquid in the container is dominated by surface adhesion, rather than gravity. If the volume of the liquid in the container is only a few nano-liters, the liquid has high surface adhesion to the container (nanowell), so that the liquid can be regarded as stable as an adhesive attached to the bottom or the wall of the container.

Preferably, the reaction vessel may be individual reaction well(s) or pit(s) in the test slide or the assay array plate. As discussed above, it is preferably to utilize the reaction vessel of a smaller volume, ranging from several to hundreds of nano-liters, for example.

Figure 1:
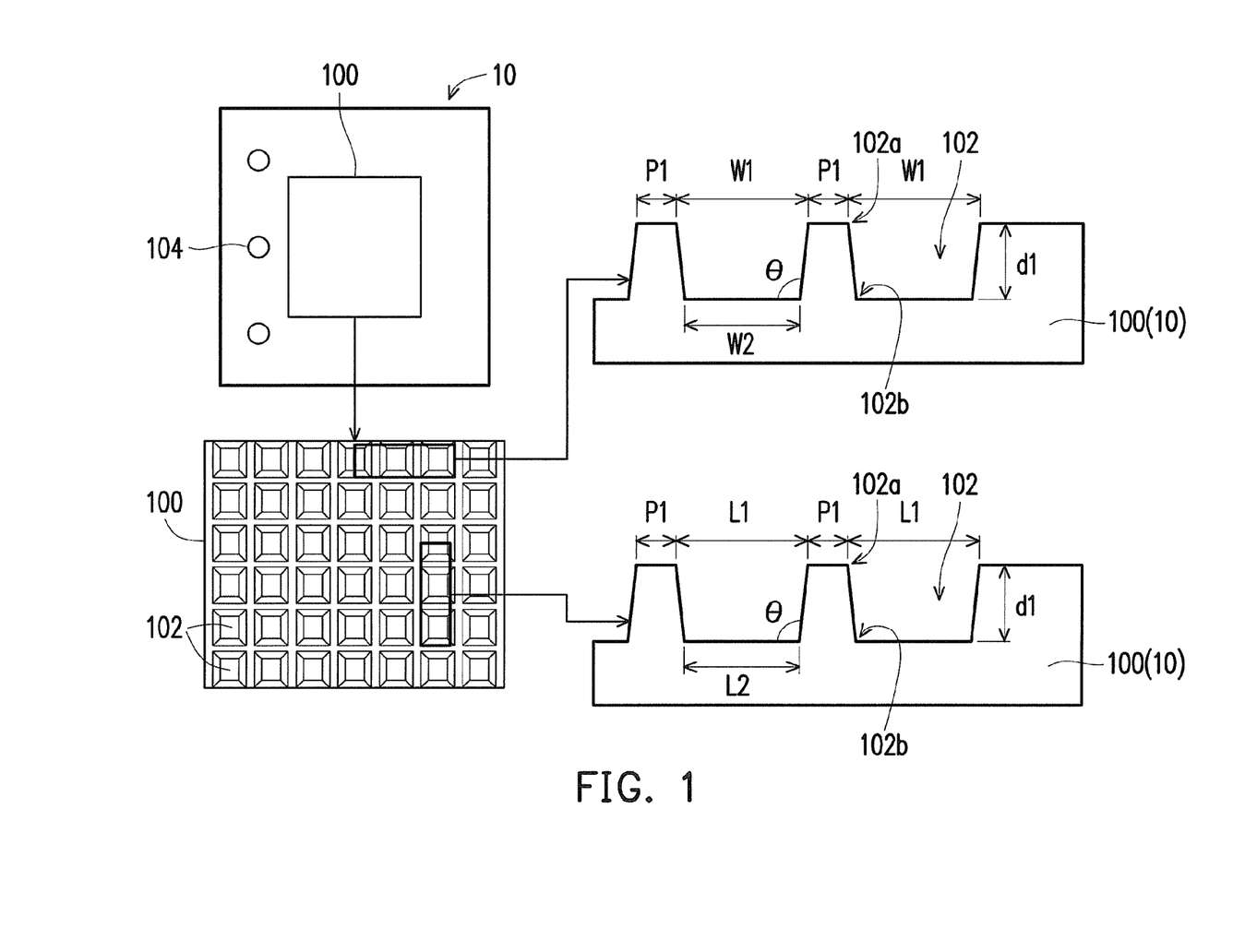
FIG. 1 is an example of an assay array plate according to one embodiment of the present invention.

FIG. 1 is an example of an assay array plate according to one embodiment of the present invention. In FIG. 1, the assay array plate (or slide plate) 10 is, for example, made of polycarbonate with the overall dimension of 36 mm×36 mm×1 mm. The assay array plate 10 has an assay region 100 contains 10,000 reaction vessels (nanowells) 102 arranged in a 100-by-100 array covering the area of 22.5 mm×22.5 mm. The assay array plate 10 also has sample loading sites 104. From the cross-sectional views (right part of FIG. 1) of the array plate 10, the nanowell 102 may be wide in the opening portion 102*a* and narrower in the bottom portion 102*b*. Each rectangular nanowell 102 has a dimension of 100 microns (d1) in depth with 200 microns (L1)×185 microns (W1) for the opening portion 102*a* and has a dimension of 106.74 um (L2)×91.74 um (W2) for the bottom portion 102*b*. The pitch (p1) or distance between the nanowells may range from 25~40 microns, and the slanted sidewall of the nanowell 102 may has an angle θ greater than 90 degrees, more preferred between 100 to 135 degrees, more preferred of 110 to 120 degrees, for example. Each nanowell 102 may accommodate 2.1 nano-liters of sample solution, for example.

FIG. 1' shows exemplary cross-sectional views of the reaction vessels of the assay array plate according to embodiments of the present invention. In FIG. 1', the reaction vessels of the assay array plate 10 may be designed with different shapes or profiles. For example, the nanowells 160*a*-160*b* are concave cavities formed within the assay array plate 10 but not penetrating through the assay array plate 10. The nanowells 160*b*, 160*d*, 160*f* have slanted sidewalls. The nanowells 160*c*-160*f* penetrate through the assay array plate 10 and have two open ends at the top and bottom surfaces of the assay array plate 10. Due to the capillary action, the sample liquid is steadily hold in the nanowells 160*c*~160*f*. The nanowell 160*d* has two open ends at the top and bottom surfaces of the assay array plate 10 and has slanted sidewalls connecting the two open ends.

The shape, size or number of the nanowells is not limited to the example. The cross-sectional shape of the nanowell may be a circle, square or polygon, for example.

Generally, as the primers are soluble in aqueous solvents or solutions, the test slide of the present invention may be designed to be hydrophilic in the inner wall and the bottom surface of the reaction zone (well), and to be hydrophobic in the regions between the reaction zone (well). The prefilled reagent(s) or probe(s) will be attached only to the hydrophilic regions, that is, the inner wall and the bottom surface of the reaction zone (well). The size of each reaction vessel or well may be less than 1 mm. In this scale, small amounts of sample fluid can overflow large numbers of reaction vessels in 10 seconds, significantly improving sample loading efficiency.

Figure 2:
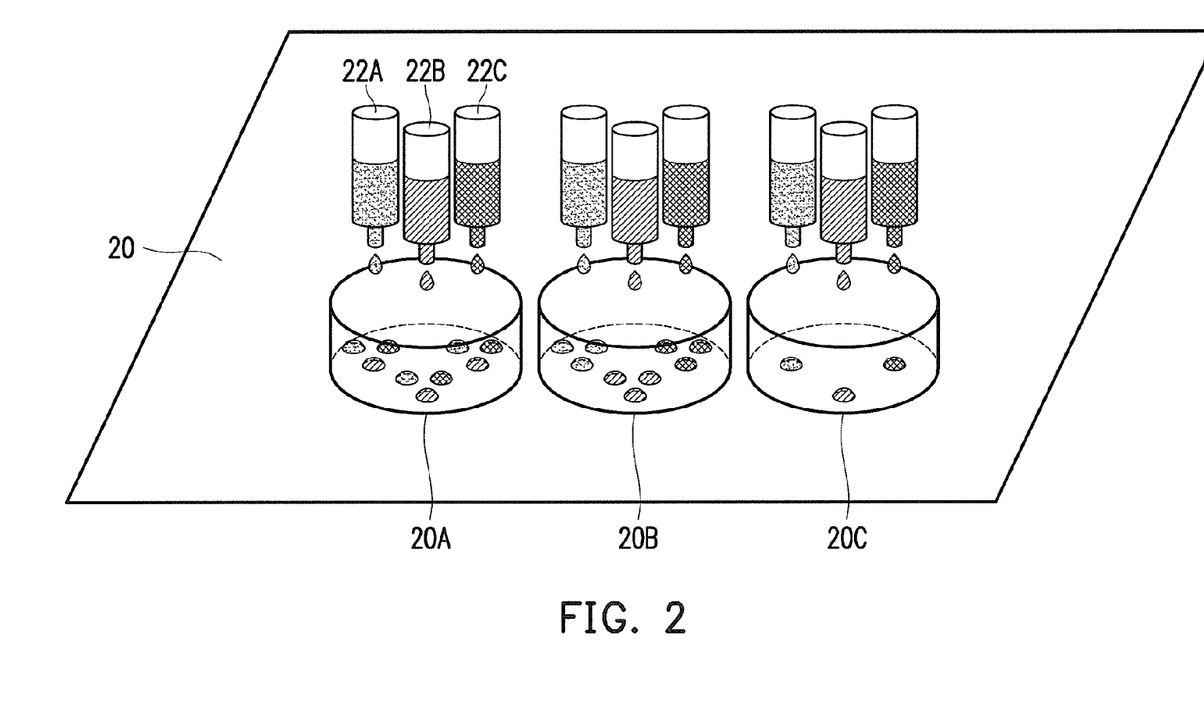
FIG. 2 shows the dispensing of the pre-filled reagent(s) according to one embodiment of the present invention.

The pre-filled reagent(s) may be loaded to the reaction vessel or reaction wells by pipetting or through any possible liquid or gel dispenser. FIG. 2 shows the dispensing or loading of the pre-filled reagent(s) according to one embodiment of the present invention. The pre-filled reagent is prepared to include one or more of the assay reagents mixing with the controlled-release recipe. The pre-filled reagent(s), shown in FIG. 2 as a liquid solution, may be dropped or loaded into three reaction compartments 20A, 20B, 20C of the assay array plate 20 through different dispensers 22A, 22B, 22C. The assay array plate 20 is then ready for storage or shipment. As shown in FIG. 2, in the reaction compartments 20A, 20B and 20C, different dispensing patterns are presented, as the dispensing patterns of different reagent(s) may affect the controlled release rate or release ratios of the ingredients.

Loading of the sample may be performed by overflow, immersion, capillary suction, vacuum suction, brushing or squeegee over the reaction slide plate. The overflow method refers to overflowing or flooding the reaction zone(s) with the sample to fill up the reaction zone(s). The immersion method refers to soaking the test slide with the reaction vessels or wells into the sample solution to fill up the reaction vessels or wells. For the capillary suction method or the vacuum suction method, the sample can be filled into the reaction zone or vessels through capillarity reaction or vacuum suction. The brushing method or the squeegee method refers to driving or pushing the sample to a number of reaction wells simultaneously through the brusher or squeegee.

Figure 3A:
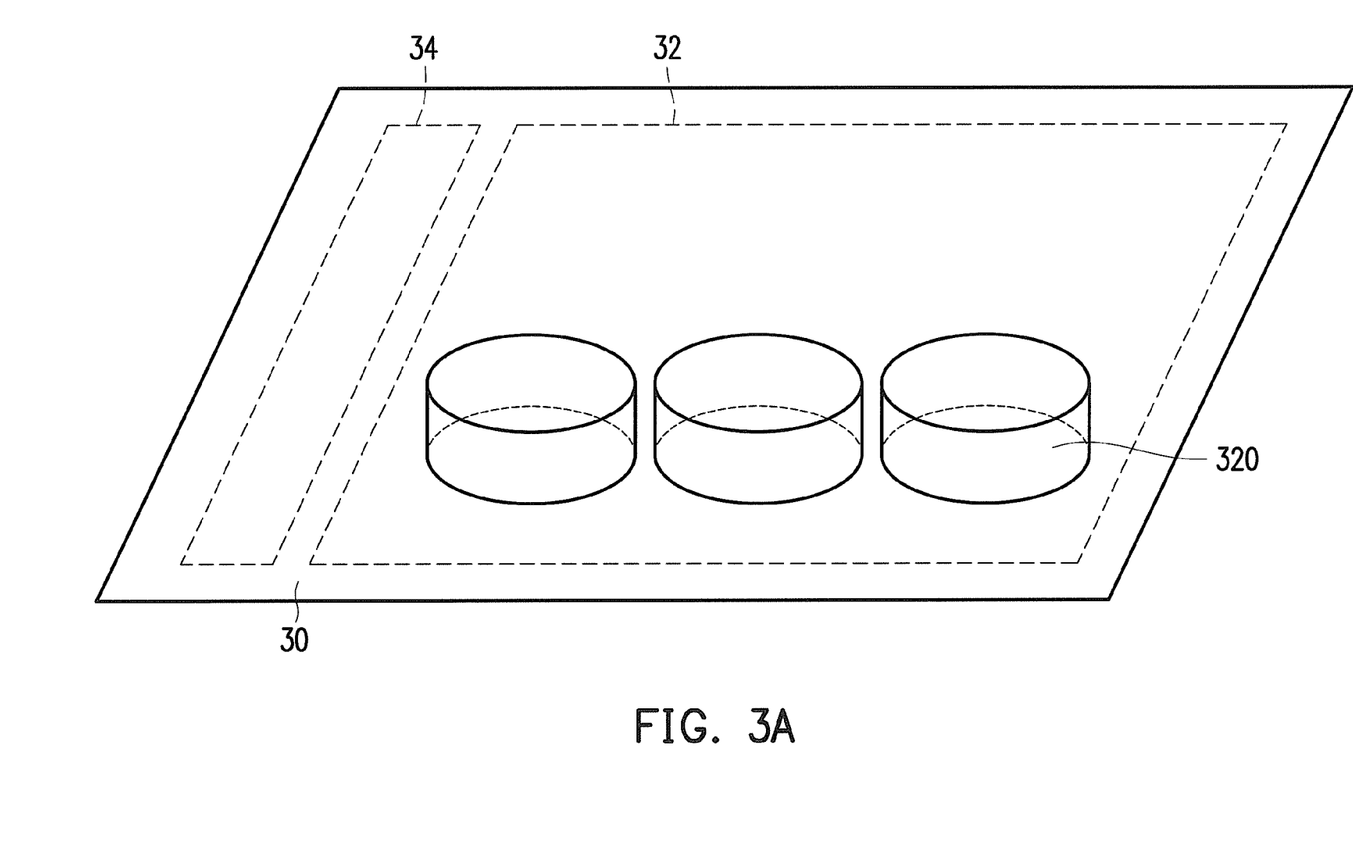
FIGS. 3A-3E show the application process steps of the assay according to the embodiment of the present invention.
Figure 3B:
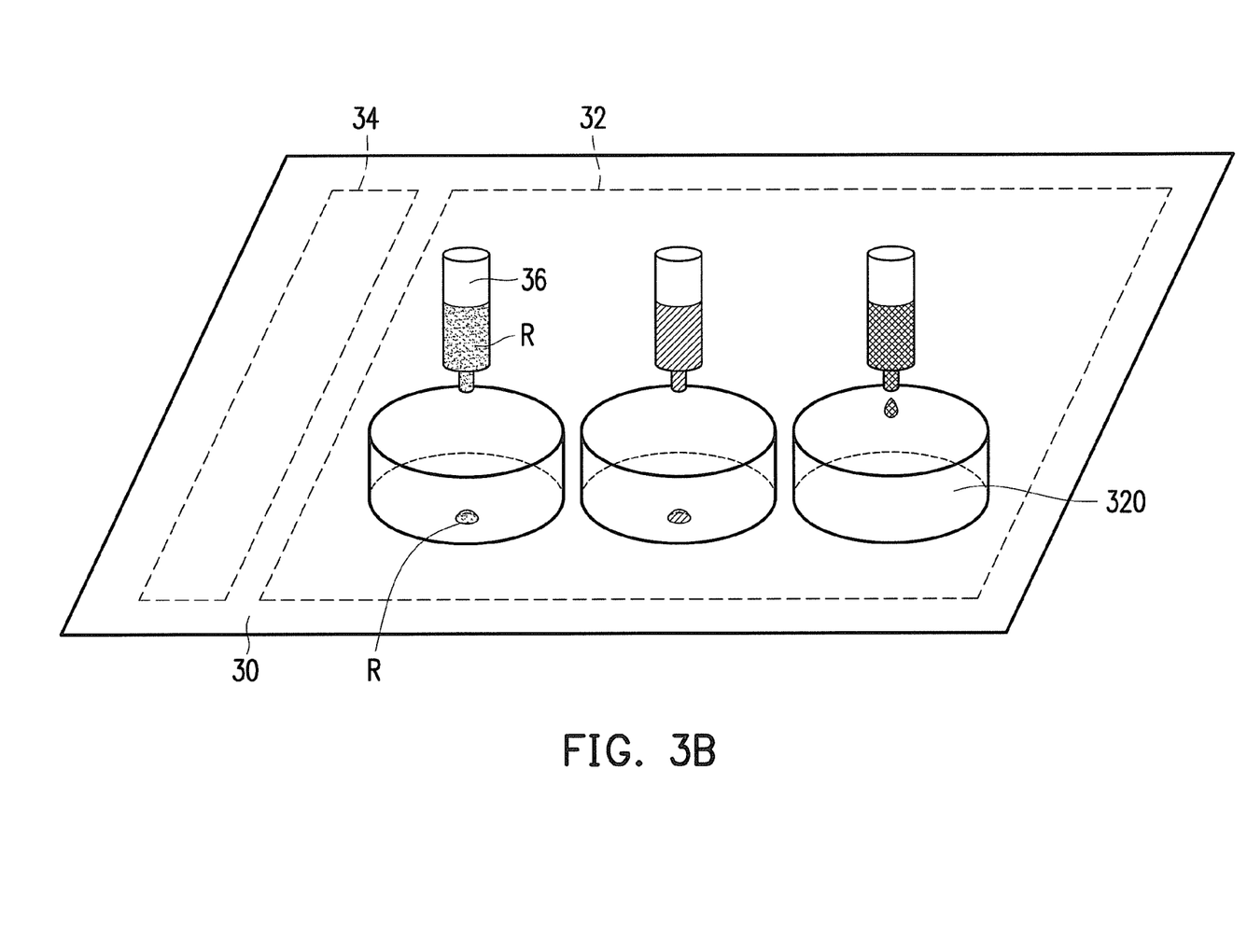
Figure 3C:
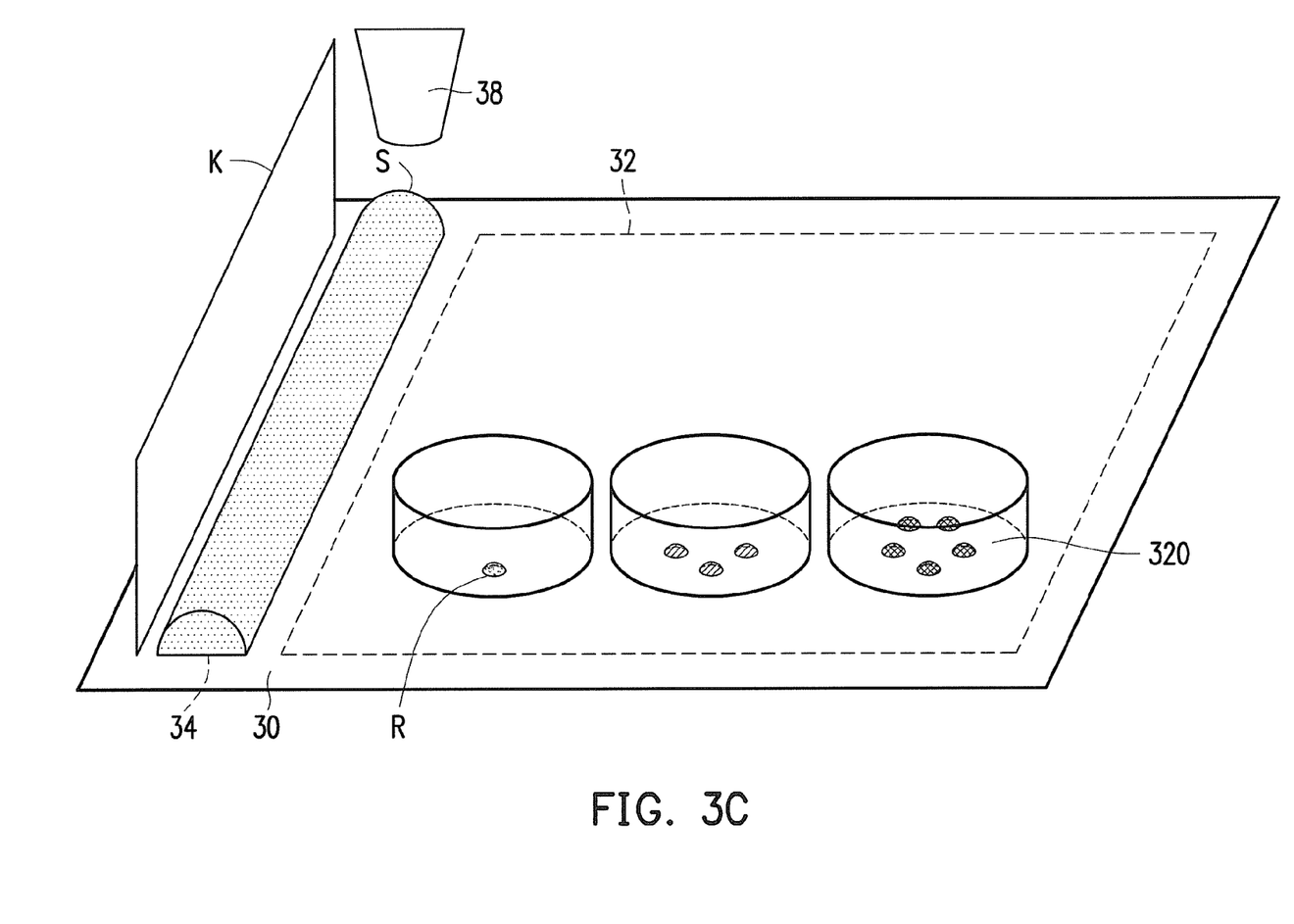
Figure 3D:
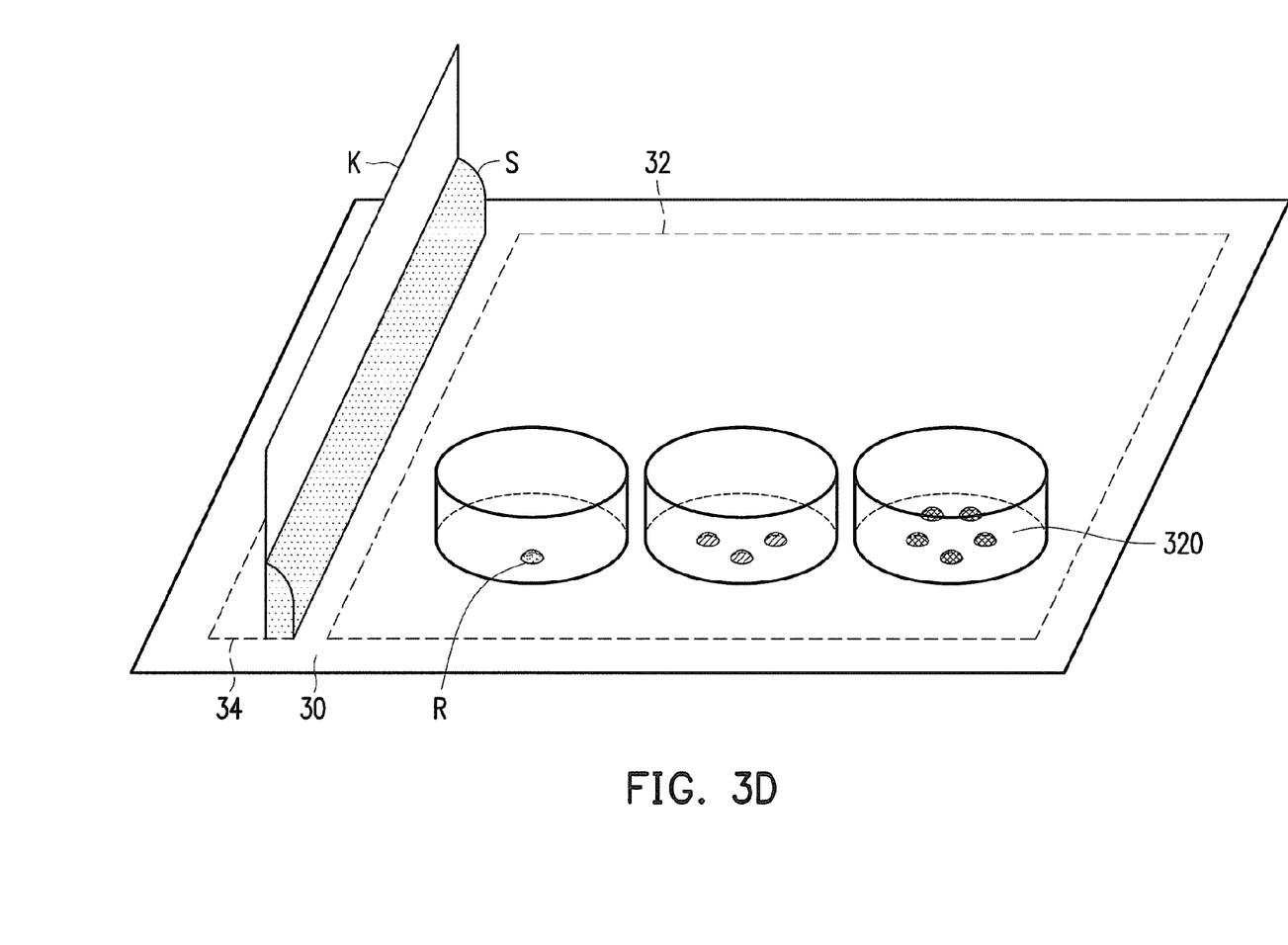
Figure 3E:
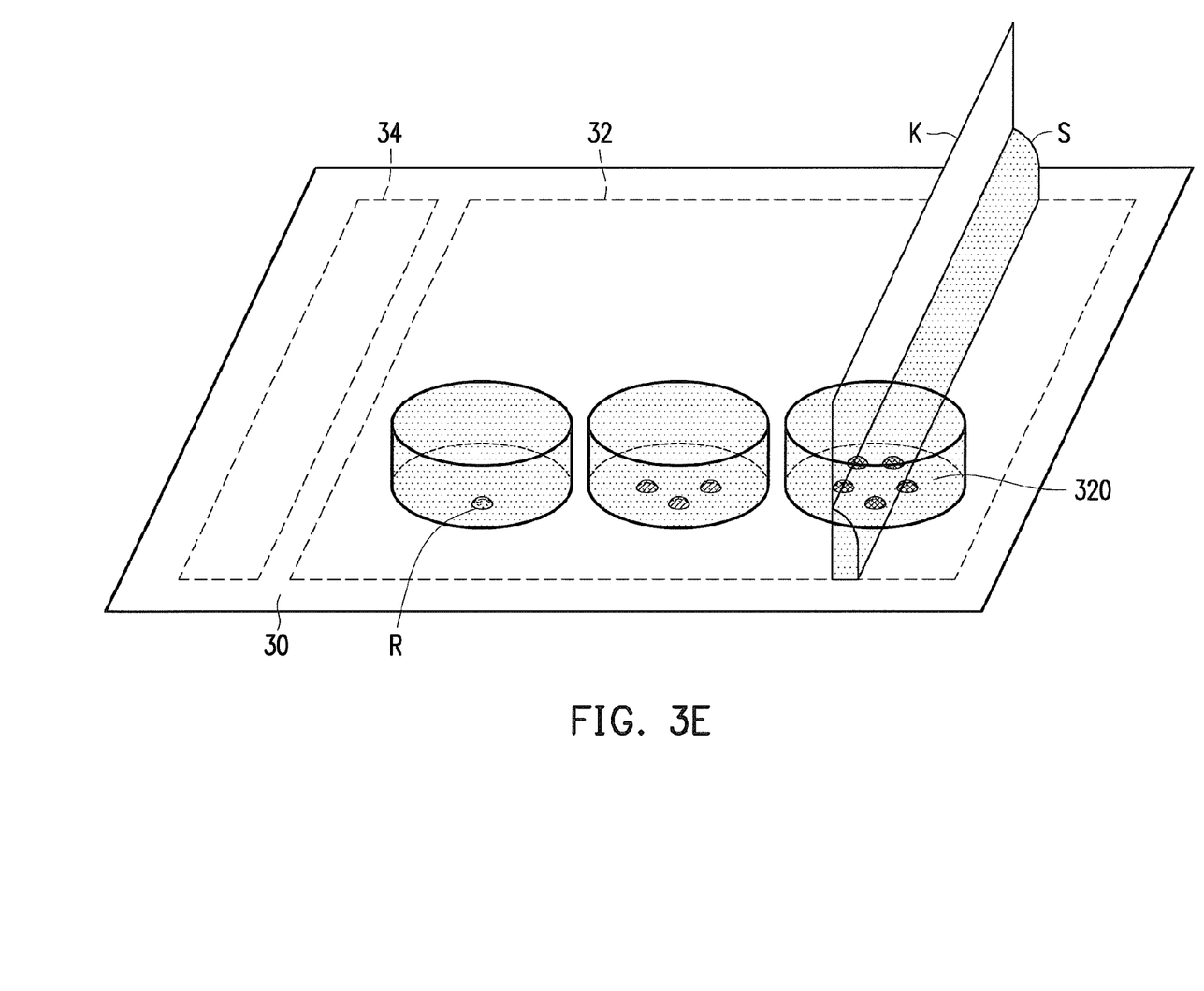

FIGS. 3A-3E show the application process steps of the assay according to the embodiment of the present invention. In FIG. 3A, the assay array plate 30 is provided with an assay region 32 having a plurality of reaction wells 320 and a sample loading region 34. In FIG. 3B, the pre-filled reagent R is loaded by the dispenser 36 into the reaction wells 320. In FIG. 3C, the sample S is loaded to the sample loading region 34 by the sample loading device 38. In FIGS. 3D-3E, the sample S is pushed by the squeegee K over the assay region 32 of the array plate 30, so that the sample S is filled into the reaction wells 320. After the sample S is in contact with the pre-filled reagent R, the pre-filled reagent R starts to dissolve and releases the specific primer fluorescent reporters or reagent(s) into the sample solution. Then the assay reaction can be initiated under the desirable conditions of the assay reaction.

Several reagents can be per-filled to the same reaction well for multiple reactions.

During loading the sample, the sample may covers all of the reaction zones, and during a short period (the flooding period), the sample links all or several reaction zones. Release control refers to the design of the release a specific component in a controlled way. For example, the specific component is enveloped, dissolved or adsorbed on or in a viscous carrier, a solid or liquid, so that it can be released at a particular timing. The formulation of the pre-filled primer pairs is designed not to dissolve (or only dissolve a little) during the flooding period or until the flooding period is over. The release mechanism of release control may be triggered by the temperature, the ultrasound or photolysis reaction or through the encapsulating or enveloping formulation of long time dissolution.

By adjusting the diluent formulation of the reagent(s) or primer(s) in the present invention, the reagent(s) or primer(s) may include at least one volatile component, at least one low-volatile component and at least one viscous component. Before placing the reagents) or primer(s) in the reaction zone, sufficient fluidity, provided by high content of the volatile component(s), is required to allow dispensing the reagent(s) or primer(s), through either direct-contact or non-direct-contact type mechanism, and allow transferring the liquid to the desired reaction zone. Once the reagent(s) or primer(s) is loaded in the reaction zone, the volatile component(s) is reduced via volatilization thereof, thus decreasing fluidity and mobility of the reagent liquid to a set and viscous state. Water or volatile solvents of the pre-filled test reagents may be partial or completely removed for shipping or transportation conveniences. However, because it contains non-volatile or low-volatile components, the reagent liquid will not be completely dried up, thereby preventing peeling or flaking due to excessive drying.

The dissolution rate of the gel-like reagent(s) or primer probe(s), when exposure to the sample liquid, is limited by the limited mass transfer surface and is pretty slow, without stirring or heating. However, the loading or filling of the sample may be completed in a matter of seconds, so that the cross-contamination of the reaction zones with different primer is avoided.

Release Control Formulation

The non-volatile or low-volatile component used in the present invention may be substances of high water solubility and viscosity and low volatility, such as sugars, carbohydrates, glycerol, oligosaccharides, polysaccharides, alcohols. After the reagent(s) or primer(s) is pre-filled in the reaction zone, the volatile component, such as water, of the formulation gradually evaporates and the content of non-volatile or low-volatile components gradually increases. Such phenomenon enhances the inhibition of biochemical reactions and is beneficial for slide preservation. If glycerol is used as the non-volatile component, for example, after evaporation of the volatile components, the content of glycerol may be increased to 30% by weight or more. This concentration of glycerol inhibits biochemical reactions for better long-term preservation.

In order to achieve controlled release effect, the controlled-release substance is added in the formulation of the prefilled reagent(s), which may be referred as the release control formulation of the prefilled reagent(s). The controlled-release substance includes long chain polymer compounds, colloid-forming components, components capable of forming a porous structure, components adsorptive to the reagent(s) to be slowly-released, components capable of bonding with the reagent(s) to be slowly-released or the combinations thereof.

The colloid-forming component may be poly(vinyl alcohol) (PVA), poly(vinyl pyrrolidone)(PVP), polyethylene glycol/polyethylene oxide (PEG/PEO), which is to form a polymer gel. After dried up, it takes time to completely dissolve when in contact with water. Alginic acid, also called algin or alginate, is an anionic polysaccharide can be used under the appropriate conditions to form a gel. In addition, natural or artificial starch may be used as the colloid-forming component or the controlled-release substance.

The component capable of forming a porous structure after filled into the reaction vessel may be, for example, polyurethane, agarose and polyacrylamide. Such substance can form a micro-porous structure to fill with the reaction vessel.

The components adsorptive to the reagent(s) to be slowly-released may be liposomes, micron particles or nano-particles, such as activated carbon particles.

The components capable of bonding with the reagent(s) to be slowly-released may be compound(s) that is reacted with the entire or partial surface of the reaction vessel to modify the surface with high affinity to the reagent(s) to be slowly-released. That is, such component can modify the surface of the reaction vessel to have a high affinity or adsorption toward the reagent(s) to be slowly-released, for controlled-release effect. After loading the sample, such affinity or adsorption may be reversed to release the reagent for the reaction. The affinity or adsorption may be reversed by changing pH, salinity, temperature, enzymatic reactions, chemical reactions, photochemical reactions of the liquid in the reaction vessel, thus reducing its affinity or its bonding.

Preparation of the Assay Array Plate with the Pre-Filled Reagent(s)

To achieve the recipe of controlled release, the reagent may be mixed with the controlled-release substance using water or volatile solvents, and pre-filled into the reaction well (reaction vessel). After removing water or volatile components, the mixture becomes a solid or a semi-solid or a gel-like form. The reagent(s), such as the PCR primer, is dispersed in the controlled-release substance (as the matrix) in a semi-solid or gel-like state. When the sample is applied to the reaction wells, the reagent(s) is slowly released due to slow dissolution of the filling matrix substance.

Alternatively, the reagent(s), in a liquid state, is pre-filled into the reaction well (reaction vessel), and the controlled-release substance is then filled into the reaction well. After removing the volatile component or water, the mixture becomes a solid or a semi-solid or a gel-like form, suitable for preservation.

Alternatively, the controlled-release substance, in a liquid state, is pre-filled into the reaction well (reaction vessel), and the reagent(s) is then filled into the reaction well. After removing the volatile component or water, the mixture becomes a solid or a semi-solid or a gel-like form.

On the other hand, the reagent(s) is pre-filled into the reaction well (reaction vessel) and dried. Then, the controlled-release substance is filled into the reaction well by spraying, injection or coating, to cover the dried reagent(s). After removing water or the volatile component from the controlled-release substance, the mixture becomes a solid or a semi-solid or a gel-like form.

In addition, the reagent(s), in a liquid state, is pre-filled into the reaction well (reaction vessel), and the dried powders of the controlled-release substance are then sprayed into the reaction well to cover the reagent(s) to form a controlled-release film.

Example I (1) preparing 20~200 µM of the primer DNA aqueous solutions used in each assay; (2) dispensing the primer DNA aqueous solutions in various quantities to predetermined reaction wells of the assay array plate; (3) placing the assay array plate filled with the primer DNA aqueous solutions in the oven at 60° C. for 1~24 hours; (4) preparing 1%~20% of a water-soluble polymer solution (e.g. PVA, PEG, polyester, gelatine and agarose) solution; (5) removing the dried assay array plate (test slide) from the oven, and loading the water-soluble polymer solution into the reaction wells by a blade; and (6) placing the assay array plate filled with the water-soluble polymer solution in the oven at 60° C. until dried up. The dried water-soluble polymer solution will form a water-soluble film on the primer DNAs. When the reaction solution and the sample solution are introduced, the water-soluble polymer film will dissolve slowly to release the primer DNA, thus avoiding cross-contamination caused by immediate dissolution of the primer DNA.

Example II (1) preparing 20~200 µM of the primer DNA aqueous solutions used in each assay; (2) dispensing the primer DNA aqueous solutions in various quantities to predetermined reaction wells of the assay array plate; (3) placing the assay array plate filled with the primer DNA aqueous solutions in the oven at 60° C. for 1~24 hours; (4) preparing a paraffin solution (paraffin wax soluble in n-hexane); (5) removing the dried assay array plate (test slide) from the oven, and loading the paraffin solution into the reaction wells by a blade; and (6) vacuum drying the assay array plate filled with the paraffin solution under heating for removing solvents. The dried paraffin solution will form a film on the primer DNAs. When the reaction solution and the sample solution are introduced at room temperatures, the paraffin film will prevent the primer DNA from being released. After heating, the paraffin melts slowly to release the primer DNA, thus avoiding cross-contamination caused by immediate dissolution of the primer DNA.

Example III (1) preparing 20~200 μM of the primer DNA aqueous solutions used in each assay; (2) dispensing the primer DNA aqueous solutions in various quantities to predetermined reaction wells of the assay array plate; (3) placing the assay array plate filled with the primer DNA aqueous solutions in the oven at 60° C. for 1~24 hours; (4) preparing 1%~20% of a water-soluble polymer solution (e.g. PVA, PEG, polyester, gelatine and agarose) solution; (5) removing the dried assay array plate (test slide) from the oven, and loading the water-soluble polymer solution in the form of micro-droplets by ultrasound into the reaction wells; and (6) drying up the assay array plate filled with the water-soluble polymer solution in the oven or by vacuum drying. The dried water-soluble polymer solution will form a water-soluble film on the primer DNAs. When the reaction solution and the sample solution are introduced, the water-soluble polymer film will dissolve slowly to release the primer DNA, thus avoiding cross-contamination caused by immediate dissolution of the primer DNA.

Example IV (1) preparing 20~200 μM of the primer DNA aqueous solutions used in each assay; (2) dispensing the primer DNA aqueous solutions in various quantities to predetermined reaction wells of the assay array plate; (3) placing the assay array plate filled with the primer DNA aqueous solutions in the oven at 60° C. for 1~24 hours; (4) preparing 1%~20% of a water-soluble polymer solution (e.g. PVA, PEG, polyester, gelatine and agarose) solution; (5) placing the dried assay array plate (test slide) on the hot plate, and loading the water-soluble polymer solution in the form of micro-droplets by spray device into the reaction wells. The micro-droplets dry up through evaporation and become polymer particles when reached the reaction wells. The dried water-soluble polymer particles will cover the primer DNAs. When the reaction solution and the sample solution are introduced, the water-soluble polymer particles will dissolve slowly to release the primer DNA, thus avoiding cross-contamination caused by immediate dissolution of the primer DNA.

Example V (1) preparing 20~200 μM of the primer DNA aqueous solutions used in each assay; (2) dispensing the primer DNA aqueous solutions in various quantities to predetermined reaction wells of the assay array plate; (3) placing the assay array plate filled with the primer DNA aqueous solutions in a chamber with a paraffin block and heating to generate wax vapor from the paraffin block. The paraffin wax vapor evenly penetrates into the micro reaction wells, attaches to the surface of the primer DNA to form a thin film. When the reaction solution and the sample DNA solution are introduced at room temperature, the paraffin wax film prevents the primer DNA from being released. After heating, the paraffin film melts slowly to release the primer DNA, thus avoiding cross-contamination caused by immediate dissolution of the primer DNA.

Example VI (1) preparing 1%~20% of a water-soluble polymer solution (e.g. PVA, PEG, polyester, gelatine and agars) solution and loading the water-soluble polymer solution into the predetermined reaction wells of the assay array plate by a blade; (2) preparing 20~200 μM of the primer DNA aqueous solutions used in each assay; (3) dispensing the primer DNA aqueous solutions in various quantities to the reaction wells of the assay array plate filled with the water-soluble polymer solution; (4) placing the assay array plate filled with the primer DNA aqueous solutions in the oven at 60° C. for 1~24 hours; and (5) removing the dried assay array plate (test slide) from the oven. The dried water-soluble polymer solution will form a water-soluble film on the primer DNAs. When the reaction solution and the sample solution are introduced, the water-soluble polymer film will dissolve slowly to release the primer DNA, thus avoiding cross-contamination caused by immediate dissolution of the primer DNA.

Example VII (1) preparing 20~200 μM of the primer DNA in an aqueous solution containing 1%~20% of the controlled-release substances (such as PEG, PVA or glycerol); (2) dispensing the primer DNA aqueous solution containing the controlled-release substances to the reaction wells of the assay array plate; and (3) placing the assay array plate filled with the primer DNA aqueous solution containing the controlled-release substances in the oven at 60° C. for 1~24 hours. When the reaction solution and the sample solution are introduced, the dried primer DNA will not be released immediately but controlled-released for at least 10 seconds. The slowly released primer DNA avoids cross-contamination.

Figure 4A:
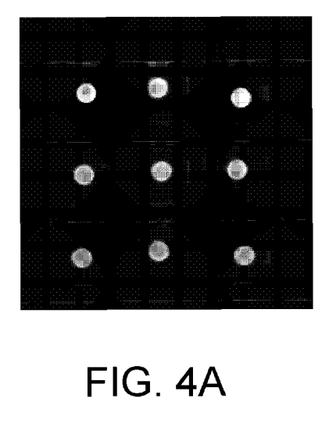
FIG. 4A shows the fluorescence signals of the pre-filled reagent(s) with the fluorescent dye and glycerol in the reaction vessels of the present invention.
Figure 4B:
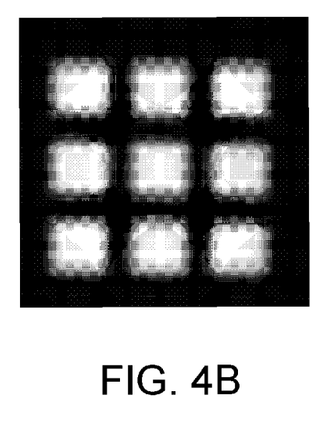
FIG. 4B shows the fluorescence signals after loading the sample solution to the reaction vessels having the pre-filled reagent(s) with the fluorescent dye and glycerol.
Figure 4C:
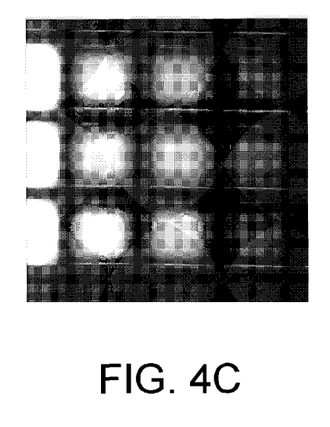
FIG. 4C shows the fluorescence signals after loading the sample solution to the reaction vessels having the pre-filled reagent(s) with the fluorescent dye but without glycerol.
Figure 4D:
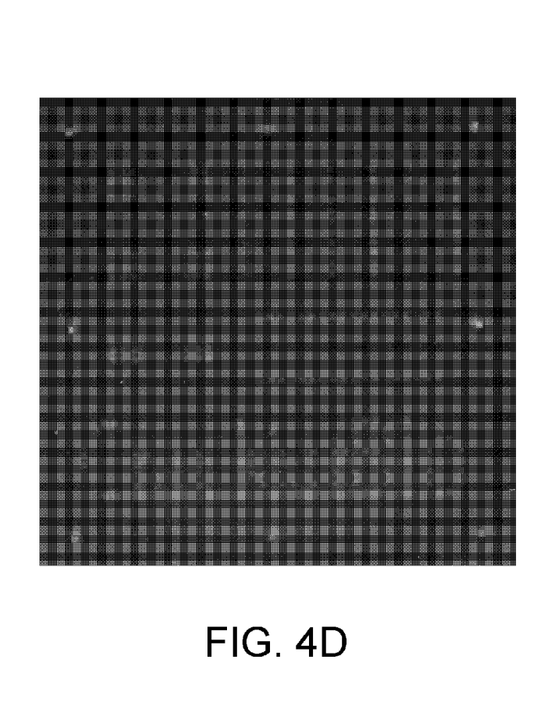
FIG. 4D shows the fluorescence signals after PCR of 40 thermal cycles from the reaction vessels loaded with the sample solution and the pre-filled reagent(s) with the fluorescent dye and controlled-release substance.
Figure 4E:
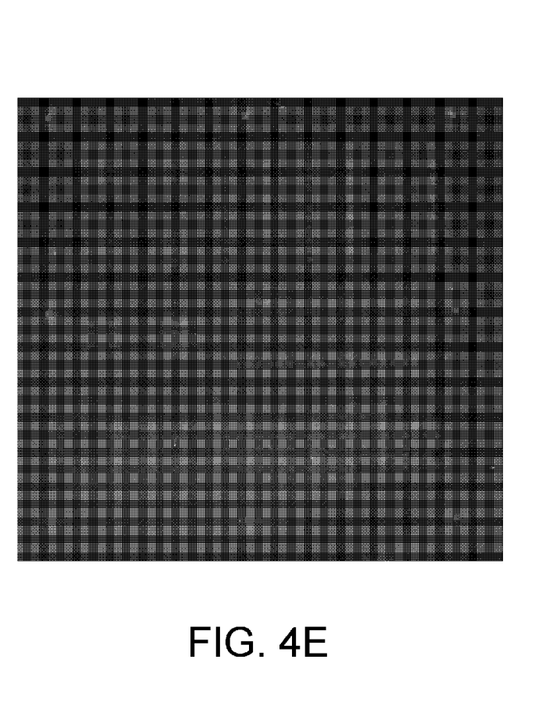
FIG. 4E shows the fluorescence signals after PCR of 40 thermal cycles from the reaction vessels loaded with the sample solution and the pre-filled reagent(s) with the fluorescent dye but without controlled-release substance.

FIG. 4A shows the fluorescence signals of the pre-filled reagent(s) with the fluorescent dye and glycerol in the reaction vessels of the present invention. FIG. 4B shows the fluorescence signals after loading the sample solution to the reaction vessels having the pre-filled reagent(s) with the fluorescent dye and glycerol. FIG. 4C shows the fluorescence signals after loading the sample solution to the reaction vessels having the pre-filled reagent(s) with the fluorescent dye but without glycerol. FIG. 4D shows the fluorescence signals after PCR of 40 thermal cycles from the reaction vessels loaded with the sample solution and the pre-filled reagent(s) with the fluorescent dye and controlled-release substance (glycerol). FIG. 4E shows the fluorescence signals after PCR of 40 thermal cycles from the reaction vessels loaded with the sample solution and the pre-filled reagent(s) with the fluorescent dye but without controlled-release substance.

For the experiments of FIGS. 4A and 4B, the pre-filled reagent solution contains 15 wt % glycerol (as the controlled-release substance) in water with fluorescent dye Alexa488 (8 μM) for checking the cross-contamination during the sample loading. As shown in FIG. 4A, the pre-filled reagent solution was deposited repeatedly into 9 nanowells (3×3). The droplets of the pre-filled reagent solution were located on the bottom surface of the wells and the content of glycerol may be increased to 30 wt % or more after the volatile component (water) evaporated. The droplets, after water evaporated, become viscous with a gravity sliding rate less than 5 μm/day and adhere to the bottoms or sidewalls of the wells. These droplets (shown as round spots in FIG. 4A) remained immobilized in the nanowells during a 30-day period of observation. The pre-dispensed assay array plate is then loaded with the sample solution by smearing the solution across the surface of the assay array plate. The sample solution may contain the standard PCR reaction mixtures, including dNTPs, MgCl$_2$, and Taq DNA polymerase, etc. As shown in the FIG. 4B, the uniform distribution of the fluorescence (i.e. fluorescent dye) within the nanowells indicates the pre-filled reagent is completed dissolved into the sample solution after brief heating at 90~92° C. for 1 minute. For example, the pre-filled reagent has a dissolution rate of 90% or more in one minute under 90° C. and a dissolution rate of 1% per second (%/sec) or less at room temperature.

Between the adjacent nanowells, no detectable differences in fluorescent signals were observed. As the controlled-release control effect is observed for the nanowells, no cross-contamination may occur during the loading of the sample solution.

In contrast, in the experiment of FIG. 4C, the pre-filled reagent solution containing no glycerol completely dried up shortly after being deposited into the nanowells. As shown in FIG. 4C, the three columns of nine nanowells are dispensed with the pre-filled reagent solution having the fluorescent dye without glycerol, and the sample solution was loaded by smearing across the nanowells array from left to right. After loading the sample solution, the fluorescent signal was immediately detected in the three nanowells of the first column on the left. The fluorescence intensity detected in the nanowells decreases from left column to right column. As no controlled-release control effect is observed, it is unlikely to avoid cross-contamination. This experiment demonstrates the importance of using control-release recipe in the pre-filled reagent solution.

Similarly, compared with the distinct fluorescent patterns (bright round spots in arrays, lines or arranged as letters) shown in FIG. 4D, it is observed in FIG. 4E that vague fluorescent signals are seen around the distinct fluorescent patterns, which indicates cross-contamination occurs during sample loading for the reaction vessels having the prefilled reagents without the controlled-release substance.

In summary, through a specific formulation of the pre-filled reagents in the present invention, the reagent probes placed in advance are viscous enough to adhere to the inner wall or bottom surface of the reaction zone, with minimal flow or peeling for better long-term storage and convenient transportation. The specially formulated reagent(s) is controlled-released so that the prefilled primer probes will not be released during filling the sample(s). During filling the sample, the sample covers all of the reaction zones, and the sample at a very short time links all or several reaction zones (i.e. all or several reaction zones are actually interconnected). By doing so, cross-contamination of the primer probes between the reaction zones will not happen because the reactions carried out independently in separate reaction zones.

The sample may also be loaded to the test slide by immersing the test slide piece into the sample solution, so that the sample is automatically and rapidly filled into each reaction zone. Then, the test slide pieces are pulled out from the sample solution. During the sample filling process, due to the controlled release properties of the prefilled reagents, reaction independence of each reaction zone is still maintained.

It will be apparent to those skilled in the art that various modifications and variations can be made to the structure of the disclosure without departing from the scope or spirit of the disclosure. In view of the foregoing, it is intended that the disclosure cover modifications and variations of this disclosure provided they fall within the scope of the following claims and their equivalents.

What is claimed is:

1. A multiplex slide plate, comprising:
a slide plate having a plurality of reaction vessels, wherein the plurality of reaction vessels is arranged in arrays and each of the plurality of reaction vessels has an opening portion and a bottom portion, and
wherein each of the plurality of reaction vessels includes a formulation of a mixture of a prefilled reagent and a controlled-release substance, and the formulation of the mixture of the prefilled reagent and the controlled-release substance allows a delayed release of the pre-filled reagent during a period of filling a sample solution to the reaction vessel, and the controlled-release substance includes glycerol, poly(vinyl alcohol) (PVA), poly(vinyl pyrrolidone) (PVP), polyethylene glycol/polyethylene oxide (PEG/PEO), alginic acid, natural starch, artificial starch, polyurethane, micron particles of activated carbon or nano-particles of activated carbon.

2. The multiplex slide plate as claimed in claim 1, wherein a formulation of the prefilled reagent includes a pair of primers of a polymerase chain reaction (PCR).

3. The multiplex slide plate as claimed in claim 2, wherein the formulation of the prefilled reagent further includes a reporter.

4. The multiplex slide plate as claimed in claim 1, wherein a content of glycerol is 30 wt % or more and a formulation of the prefilled reagent becomes viscous with a gravity sliding rate less than 5 μm/day.

5. The multiplex slide plate as claimed in claim 1, wherein the slide plate is made of polycarbonate (PC) or poly(methyl methacrylate) (PMMA).

6. The multiplex slide plate as claimed in claim 1, wherein each of the plurality of reaction vessels has a slanted sidewall connecting the opening portion and the bottom portion and has an angle θ of greater than 90 degrees, more preferred between 100 to 135 degrees, more preferred of 110 to 120 degrees, relative to the bottom portion.

7. The multiplex slide plate as claimed in claim 1, wherein the slide plate includes a sample loading region.

8. The multiplex slide plate as claimed in claim 1, further comprising a cover over the slide plate to form a close space between the slide plate and the cover.

9. The multiplex slide plate as claimed in claim 1, wherein each of the plurality of reaction vessels has two open ends.

10. The multiplex slide plate as claimed in claim 1, wherein each of the plurality of reaction vessels has two open ends, and a slanted sidewall connecting the two open ends.

* * * * *